United States Patent
Davuluri et al.

(10) Patent No.: US 9,199,916 B2
(45) Date of Patent: Dec. 1, 2015

(54) PROCESS FOR THE PREPARATION OF (R)-N-BENZYL-2-ACETAMIDO-3-METHOXYPROPIONAMIDE

(71) Applicants: Ramamohan Rao Davuluri, Hyderabad (IN); Guruswamy Batthini, Hyderabad (IN); Swetha Mustyala, Nizamabad (IN); Sudheer Kallepalli, Nalgonda (IN); Praveen Kumar Neela, Hyderabad (IN); Ravi Ponnaiah, Madurai (IN)

(72) Inventors: Ramamohan Rao Davuluri, Hyderabad (IN); Guruswamy Batthini, Hyderabad (IN); Swetha Mustyala, Nizamabad (IN); Sudheer Kallepalli, Nalgonda (IN); Praveen Kumar Neela, Hyderabad (IN); Ravi Ponnaiah, Madurai (IN)

(73) Assignee: RAMAMOHAN RAO DAVULURI (IN)

( * ) Notice: Subject to any disclaimer, the term of this patent is extended or adjusted under 35 U.S.C. 154(b) by 0 days.

(21) Appl. No.: 14/357,217

(22) PCT Filed: Nov. 8, 2012

(86) PCT No.: PCT/IN2012/000734
§ 371 (c)(1),
(2) Date: May 9, 2014

(87) PCT Pub. No.: WO2013/072936
PCT Pub. Date: May 23, 2013

(65) Prior Publication Data
US 2014/0323738 A1   Oct. 30, 2014

(30) Foreign Application Priority Data
Nov. 10, 2011  (IN) .......................... 3787/CHE/2011

(51) Int. Cl.
*C07D 263/02* (2006.01)
*C07C 231/14* (2006.01)
*C07C 231/02* (2006.01)
*C07C 231/12* (2006.01)
*C07D 263/06* (2006.01)
*C07D 263/04* (2006.01)

(52) U.S. Cl.
CPC ............. *C07C 231/14* (2013.01); *C07C 231/02* (2013.01); *C07C 231/12* (2013.01); *C07D 263/04* (2013.01); *C07D 263/06* (2013.01)

(58) Field of Classification Search
CPC .. C07D 263/04; C07D 263/06; C07D 305/14; C07D 413/12; A01N 25/32
USPC .......................................... 548/215; 564/157
See application file for complete search history.

(56) References Cited

U.S. PATENT DOCUMENTS

| 5,773,475 | A  | 6/1998  | Kohn |
| 2009/0143472 | A1 | 6/2009 | Madhra et al. |
| 2011/0130350 | A1 | 6/2011 | Riedner et al. |
| 2011/0263899 | A1 | 10/2011 | Bouvy et al. |

FOREIGN PATENT DOCUMENTS

WO    WO 2011039781 A1 *  4/2011

OTHER PUBLICATIONS

Trajkovic, M., Z. Ferjancic, and R. Saicic "A convenient procedure for the preparation of Garner's aldehyde" Tetrahedron: Asymmetry (2012), 23: pp. 602-604.*
Evindar, G., S. Bernier, E. Doyle, M. Kavarana, A. Satz, J. Lorusso, H. Blanchette, A. Saha, G. Hannig, B. Morgan "Exploration of amino alcohol derivatives as novel, potent, and highly selective sphingosine-1-phosphate receptor subtype-1 agonists" Bioorganic & Med. Chem Letter (2010), 20: pp. 2520-2524.*
International Search Report; International File Date: Nov. 8, 2012; Ramamohan Rao Davuluri et al.; 5 pgs.
Milos Trajkovic et al., A convenient procedure for the preparation of Garner's aldehyde, Tetrahedron: Asymmetry,Apr. 27, 2012, vol. 23, No. 8, pp. 602-604, See Scheme 1, experimental 3.1.2.
Ghotas Evindar et al., Exploration of amino alcohol derivatives as novel, Potent, and highly selective sphingosine-1-phosphate receptor subtype- I agonists, Bioorganic & Medicinal Chemistry Letters, Mar. 3, 2010, vol. 20, No. 8, pp. 2520-2524, See Scheme 2.

* cited by examiner

*Primary Examiner* — Nyeemah A Grazier
*Assistant Examiner* — Sagar Patel
(74) *Attorney, Agent, or Firm* — Schmeiser, Olsen & Watts, LLP

(57) ABSTRACT

The invention is a novel process for the preparation of lacosamide by employing novel intermediates of formula III and IV:

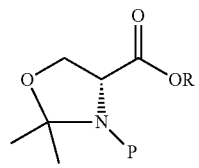

Formula III

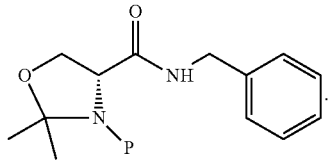

Formula IV

8 Claims, No Drawings

PROCESS FOR THE PREPARATION OF (R)-N-BENZYL-2-ACETAMIDO-3-METHOXYPROPIONAMIDE

CROSS REFERENCE TO RELATED APPLICATION

This application claims priority to PCT Application No. PCT/IN2012/000734, having a filing date of Nov. 8, 2012, based on Indian Application No. 3787/CHE/2011, having a filing date of Nov. 10, 2011, the entire contents of which are hereby incorporated by reference.

FIELD OF THE INVENTION

The present invention provides a novel process for the preparation of Lacosamide and the preparation of novel intermediates for the process of preparing Lacosamide.

BACKGROUND OF THE INVENTION

Lacosamide chemically known as (R)-N-benzyl-2-acetamido-3-methoxy-propionamideor (2R)-2-(Acetylamino)-3-methoxy-N-(phenylmethyl)propanamide of Formula I is an amino acid derivative having analgesic and anticonvulsant property.

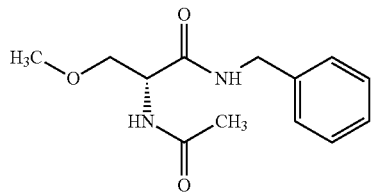

Formula I

Lacosamide was developed by UCB Pharma for the adjunctive treatment of partial-onset seizures. It is marketed under the trade name Vimpat and was approved by US FDA as an adjunctive therapy for partial-onset seizures in October 2008.

Lacosamide has been disclosed for the first time in the U.S. Pat. No. 5,773,475 by Research Corporation Technologies. According to this patent, lacosamide is prepared in three different methods. The first two methods do not involve the protection of starting material that is D-Serine is used which is converted to methyl ester followed by the reaction with benzylamine to obtain the benzylamide derivative which acetylated with acetic anhydride to obtain N-acetyl derivative. Methylation is employed with methyl iodide in the presence of silver oxide which results in Lacosamide along with the racemized product of Lacosamide.

The third method employs Cbz protected D-serine as a starting material which methylated followed by benzylation, deprotection and acetylation to obtain lacosamide. These routes are commercially not viable due to low yield since O-methylation of N-protected D-serine results in partial racemization which reduces the yield. Further the removal of S-enantiomer is difficult during production of (R)-2-acetamido-N-benzyl-3-methoxypropionamide.

An alternate method for the synthesis of Lacosamide is described in the application WO2006037574 which discloses O-methylation of N-Boc protected D-serine by employing n-Butyl lithium and dimethyl sulphate which reduces the formation of other isomer.

Another alternate method for the synthesis of Lacosamide is described in the application US20090143472 wherein the starting material employed is benzylamine amidation of N-trityl D-serine, further O-methylation, de-tritylation followed by acetylation to obtain Lacosamide. Another method involves O-methylation of N-trityl D-Serine, benzylamine amidation, detritylation and finally acetylation to obtain lacosamide.

An alternate method for the synthesis of Lacosamide is described in the application WO2010052011 wherein the racemic Lacosamide resolution to afforded R-enantiomer of Lacosamide by employing chiral chromatography.

Therefore, the present invention provides a novel process for the preparation of Lacosamide by avoiding costly reagents and the chromatography technique.

SUMMARY OF THE INVENTION

The present invention encompasses a process for preparing Lacosamide comprising of:
i) treating the compound of formula IA

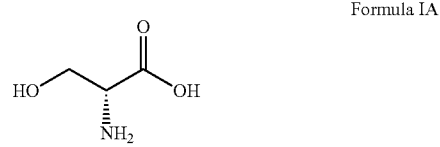

Formula IA with N-protecting groups to obtain the compound of formula II

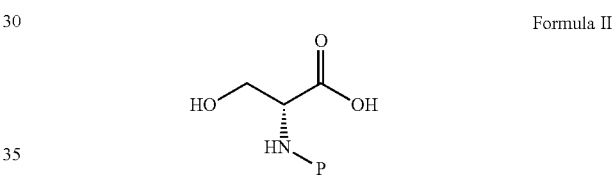

Formula II wherein P is a N-protecting group;
ii) treating the compound of formula II with 2,2-Dimethoxy propane in the presence of an acid to obtain a compound of formula III 3-(tert-butoxycarbonyl)-2,2-dimethyl-1,3-oxazolidine-4-carboxylic acid;

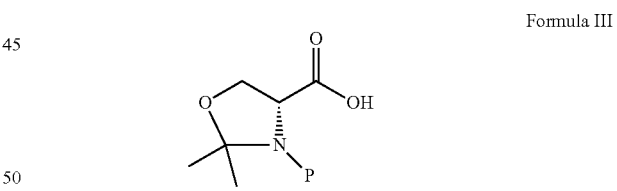

Formula III iii) treating the compound of formula III with benzylamine in the presence of a suitable base and an carboxyl activator in a suitable solvent to obtain a compound of formula IV of tert-butyl-4-(benzylcarbamoyl)-2,2-dimethyl-1,3-oxazolidine-3-carboxylate;

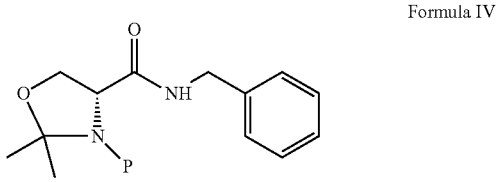

Formula IV iv) deprotecting the OH- and N-protecting groups of the compound of formula IV to obtain a compound of formula V of 2-amino-N-benzyl-3-hydroxypropanamide;

Formula V

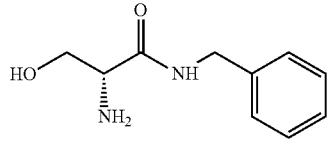

v) treating the compound of formula V with acetylating agent to obtain a compound of formula VI of 2-(acetylamino)-N-benzyl-3-hydroxypropanamide;

Formula VI

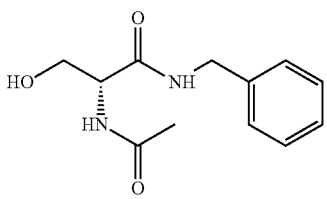

vi) treating the compound of formula VI with methylating agent in the presence of an inorganic base in an organic solvent to obtain the Lacosamide.

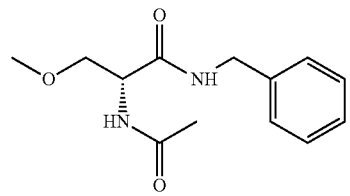 [SMILES: COC[C@@H](NC(C)=O)C(=O)NCc1ccccc1]

This process provides Lacosamide essentially free from other isomer.

The main objective of the present invention is to provide a novel and cost-effective process for the preparation of Lacosamide by employing novel intermediates.

DETAILED DESCRIPTION

A novel process for the preparation of Lacosamide by employing novel intermediates is described in this invention.

The process for the preparation of lacosamide comprising the steps of:

i) treating the compound of formula IA

Formula IA

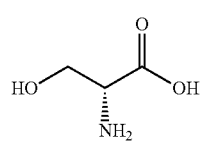

with N-protecting groups to obtain the compound of formula II,

Formula II

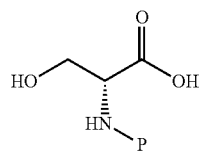

wherein P is an N-protecting group;

ii) treating the compound of formula II with 2,2-Dimethoxy propane in the presence of an acid to obtain a compound of formula III of 3-(tert-butoxycarbonyl)-2,2-dimethyl-1,3-oxazolidine-4-carboxylic acid;

Formula III

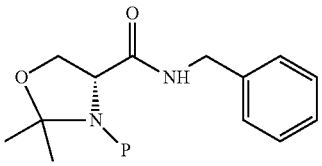

iii) treating the compound of formula III with benzylamine in the presence of a suitable base and an carboxyl activator to obtain a compound of formula IV of tert-butyl-4-(benzyl-carbamoyl)-2,2-dimethyl-1,3-oxazolidine-3-carboxylate;

Formula IV

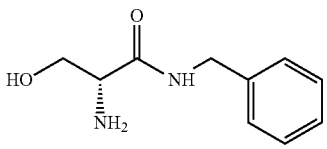

iv) deprotecting the OH- and N-protecting groups of the compound of formula IV to obtain a compound of formula V of 2-amino-N-benzyl-3-hydroxypropanamide;

Formula V

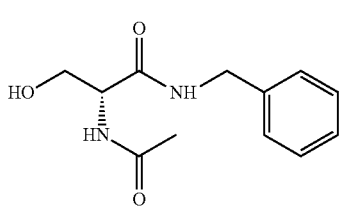

v) treating the compound of formula V with a acetylating agent to obtain a compound of formula VI of 2-(acetylamino)-N-benzyl-3-hydroxypropanamide;

Formula VI vi) treating the compound of formula VI with a methylating agent in the presence of an inorganic base in an organic solvent to obtain the Lacosamide.

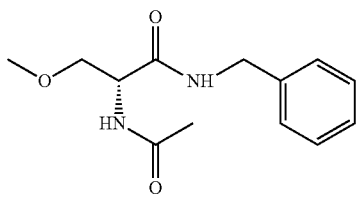 [SMILES: COC[C@@H](NC(C)=O)C(=O)NCc1ccccc1]

The acid used in the step ii) of the above process is organic or inorganic acid wherein the organic acid may be carboxylic acid or halogen substituted carboxylic acid and the inorganic acids may be hydrochloric acid, hydrobromic acid, sulfuric acid or phosphoric acid.

The base employed in step iii) of the above process is organic or inorganic base wherein the organic base is selected from the group comprising of isopropyl amine, diisopropyl amine, diisopropyl ethyl-amine, N-methyl morpholine, N-methyl piperidine, N-methyl piperazine, N-methyl pyridine, DBU, DABCO and triethylamine. Inorganic base is selected from the group comprising of alkali metals like sodium, potassium, lithium or alkali metal carbonates like sodium carbonate, potassium carbonate, cesium carbonate, lithium carbonate or alkali metal bicarbonates like sodium bicarbonate, potassium bicarbonate, lithium bicarbonate, cesium bicarbonate or alkali metal hydroxides like sodium hydroxide, calcium hydroxide, potassium hydroxide.

The carboxyl activator employed in step iii) of the above process is selected from the group of carbodiimide, alkyl chloroformate like methyl chloroformate, ethyl chloroformate, and isobutyl chloroformate.

The acetylating agent employed in step v) of the above process is selected from the group of acetic anhydride and acetyl chloride.

The methylating agent employed in step vi) of the above process is selected from the group of methyl iodide, dimethyl sulphate, dimethyl carbonate and diazomethane.

Suitable organic solvents employed to carry out the above process included but are not limited to: alcohols such as methanol, ethanol, isopropyl alcohol, isobutyl alcohol, tertiary-butyl alcohol and the like; halogenated hydrocarbons such as dichloromethane, ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran, methyl tertiary-butyl ether and the like; esters such as ethyl acetate, n-propyl acetate, isopropyl acetate, n-butyl acetate, isobutyl acetate and the like; hydrocarbons such as hexane, benzene, xylene, toluene, n-heptane and the like and aprotic polar solvents such as dimethyl sulfoxide, N,N-dimethylformamide, N,N-dimethylacetamide and the like; any solvent or mixture of solvents or their combination with water or any of the solvents from the classes mentioned.

The Nitrogen protecting groups employed herein is selected from the group of silyl, benzyl, benzoyl, carbobenzyloxy, acetyl, tosyl. The other groups known in the state of art may be employed in the process of the present invention.

The novel intermediates or its acid addition salts of the present invention may also prepared or isolated by methods known in the state of the art.

This novel process provides Lacosamide essentially free of other isomer having a purity of at least 98%.

The following examples are provided to enable one skilled in the art to practice the invention and merely illustrate the process of the invention. However, it is not intended in any way to limit the scope of the present invention.

EXAMPLES

Example 1

Preparation of Compound of Formula II

D-Serine (0.47 mol) was dissolved in water and cooled to 20-30° C. Sodium hydroxide (1.0 mol) solution was added to the reaction mixture at 20-30° C. and stirred for 45 min at the same temperature. Boc-anhydride (0.75 mol) was added to reaction mixture at 20-30° C. for 60 min. The temperature of the reaction mixture was raised up to 25-30° C. and maintained the reaction for 8 hrs. The reaction mass was filtered and separated the aqueous layer. The aqueous layer pH was adjusted to 1.0-2.0 with dilute hydrochloric acid and extracted the compound with ethyl acetate. The ethyl acetate layer was washed with sodium chloride solution, evaporated the solvent under reduced pressure to get title compound. Yield: 94%

Example 2

Preparation of Compound of Formula III

The compound of example-1 was dissolved in acetone (400 ml) and cooled to 0-5° C., $H_2SO_4$ (0.07 mol) followed by 2,2-Dimethoxy propane (1.40 mol) was added at the same temperature. The temperature of the reaction mixture was raised to 25-30° C. and maintained the reaction for 30 min, triethylamine (11.5 ml) was added and stirred for 30 min. The organic layer was separated and concentrated under reduced pressure. The resulted residue was dissolved in methylene chloride and methylene chloride layer was washed with water. Finally methylene chloride was evaporated under reduced pressure to get title compound. Yield: 88%

Example 3

Preparation Compound of formula IV

The compound of the example-2 was dissolved in methylene chloride (300 ml) and cooled to 5 ° C. N-methyl morpholine (0.27 mol) followed by isobutyl chloroformate (1.2 mol) was added at 0-10° C. and stirred the reaction mass for 1.0 hr. The benzylamine (1.2 mol) was added to the above contents at same temperature and reaction was maintained for 30-45min. The temperature of the reaction mixture was raised to 25-30° C. and stirred for 1.0 hr and filtered. The filtrate was washed with 8% sodium bicarbonate solution followed by water and solvent was evaporated under reduced pressure to get the title compound. Yield: 84%

Example 4

Preparation of Compound of Formula V

The compound of example-3 (140.0 gm) was dissolved in methylene chloride (350 ml) and hydrochloric acid (2.01 mol) was added at 25-30° C. The reaction mixture was stirred for 1.0 hr and the aqueous layer was separated, washed with methylene chloride and aqueous layer pH was adjusted to 7.0-7.5 with sodium carbonate solution at 25-30° C. and added n-heptane (140 ml). The precipitated solid was filtered and dried to get title compound. Yield: 90%

Example 5

Preparation of Compound of Formula VI

The compound of example-4 (80.0 g) was dissolved in methylene chloride (640.0 ml) and cooled to 10-15° C. The acetic anhydride (46.24 gm) was added to the reaction mixture at 10-15° C. for 15-30 min and stirred for 30 min at the same temperature. The toluene (240 ml) was added and the isolated compound was filtered and dried to get title compound. Yield: 85%

Example 6

Preparation of Lacosamide

The compound of example-5 (50.0 g) was dissolved in methylene chloride (450 ml) and cooled to 0-5° C. tetrabutyl ammonium bisulphate (2.8 g) and triethylamine (10.7 g) was added at the same temperature and dimethylsulphate (58.6 g) was added slowly for 45-60 min at 0-5° C. The reaction mass was stirred for 15 min and NaOH (15.8 g) in purified water (32.5 ml) solution was added slowly for 90 min. The reaction mass was stirred for 1.0 hr at 0-5° C. and temperature raised to 25-30° C. The reaction was maintained 4 hr at 25-30° C. and monitored the reaction by HPLC. The reaction mass was cooled to 0-5° C. ammonium chloride (25 g) in purified water (75 ml) solution followed by aqueous ammonia (125 ml) was added at 0-5° C. The reaction mass stirred for 2 hr and pH was adjusted to 7.0-7.5 with hydrochloric acid. The organic layer was separated and aqueous layer was extracted with methylene chloride (250 ml) and combined the organic layers finally washed with water. The solvent was evaporated under reduced pressure and ethyl acetate (350 ml) was added and heated the mixture to get clear solution. The reaction mass was slowly cooled to 0-5° C. and filtered the compound and dried at 50-55° C. to get (R)-2-acetamido-N-benzyl-3methoxypropionamide (lacosamide). Yield: 65%

Example 7

Purification of Lacosamide

The lacosamide (50 g) was dissolved in ethyl acetate (400 ml) at 75-80° C. and treated with activated carbon; the hot filtrate was slowly cooled to 5-10° C. and stirred for 1.0 hr at same temperature. The isolated compound was filtered and dried at 50-55° C. under reduced pressure to get pure Lacosamide. Yield: 85%

Example 8

Preparation of Lacosamide

The compound of example-5 was dissolved in acetonitrile (350 ml) at 25-30° C. and added silver oxide followed by methyl iodide and maintained the reaction for 24 hrs at 25-30° C. The reaction mixture was filtered, evaporated and the actonitrile under reduced pressure and resulted residue was dissolved in acetone. The contents were heated to reflux temperature and diisopropyl ether was added slowly at 60-65° C.

and cooled the mass to 25-30° C. and filtered the isolated compound, dried to get lacosamide. Yield: 70%

Example 9

Preparation of Lacosamide

The compound of example-5 was dissolved in acetonitrile (350 ml) at 25-30° C. and added sodium hydroxide (2.5 mol) in water solution followed by dimethyl sulphate (2.5 mol) and maintained the reaction mass 6 hr. The acetonitrile was evaporated under reduced pressure and resulted residue was dissolved in methylene chloride (250 ml). The methylene chloride layer was washed with water, and solvent was evaporated under reduced pressure. The obtained residue was dissolved in acetone (150 ml) and heated to 60-65° C. added diisopropyl ether (800 ml) and reaction mass was cooled to 25-30° C. and the isolated compound was filtered, dried to get lacosamide. Yield: 80%

Example 10

Purification of Lacosamide

The Lacosamide (50 g) was dissolved in ethyl acetate (400 ml) at 75-80° C. and treated with activated carbon; the hot filtrate was slowly cooled to 5-10° C. and stirred for 1.0 hr at same temperature. The isolated compound was filtered and dried at 50-55° C. under reduced pressure to get pure lacosamide. Yield: 85%

We claim:
1. A process for the preparation of lacosamide comprising of:
i) treating the compound of formula IA

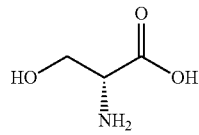

Formula IA with N-protecting groups to obtain the compound of formula II wherein P is an N-protecting group;

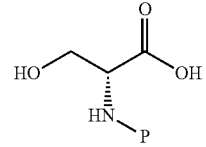

Formula II ii) treating the compound of formula II with 2,2-dimethoxy propane in the presence of an acid to obtain a compound of formula III;

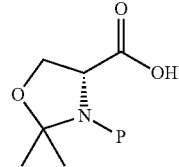

Formula III iii) treating the compound of formula III with benzylamine in the presence of a suitable base and an carboxyl activator to obtain a compound of formula IV;

Formula IV

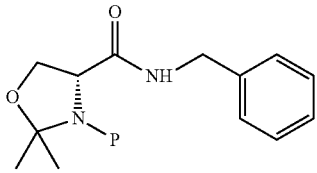

iv) deprotecting the compound of formula IV to obtain a compound of formula V;

Formula V

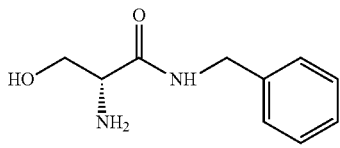

v) treating the compound of formula V with an acetylating agent to obtain a compound of formula VI;

Formula VI

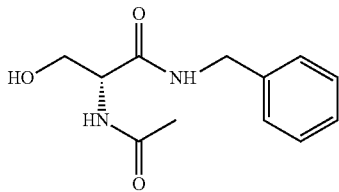

vi) treating the compound of formula VI with a methylating agent

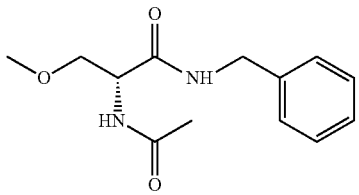 [SMILES: COC[C@@H](NC(C)=O)C(=O)NCc1ccccc1]

to obtain lacosamide.

2. The process according to claim 1, wherein the acid of step ii is selected from the group consisting of carboxylic acid, halogen substituted carboxylic acid, hydrochloric acid, hydrobromic acid, sulfuric acid and phosphoric acid.

3. The process according to claim 1, wherein the base of step iii is organic or inorganic.

4. The process according to claim 3, wherein the base is inorganic and selected from the group consisting of sodium carbonate, potassium carbonate, sodium bicarbonate, potassium bicarbonate, sodium hydroxide, potassium hydroxide and lithium hydroxide.

5. The process according to claim 1, wherein the carboxyl activator of step iii is selected from the group consisting of carbodiimide, methyl chloroformate, ethyl chloroformate, and isobutyl chloroformate.

6. The process according to claim 1, wherein the acetylating agent of step v is selected from the group consisting of acetic anhydride and acetyl chloride.

7. The process according to claim 1, wherein the methylating agent of step vi is selected from the group consisting of methyl iodide, dimethyl sulphate, dimethyl carbonate and diazomethane.

8. The process according to claim 3, wherein the organic base is selected from the group consisting of isopropyl amine, diisopropyl amine, diisopropyl ethyl-amine, N-methyl morpholine, N-methyl piperidine, N-methyl piperazine, N-methyl pyridine, DBU, DABCO and triethylamine.

* * * * *